(12) United States Patent
Shah

(10) Patent No.: US 7,682,306 B2
(45) Date of Patent: Mar. 23, 2010

(54) THERAPEUTIC INTERVENTION SYSTEMS EMPLOYING IMPLANTABLE BALLOON DEVICES

(76) Inventor: Tilak M. Shah, 104 Lochberry La., Cary, NC (US) 27511

( * ) Notice: Subject to any disclaimer, the term of this patent is extended or adjusted under 35 U.S.C. 154(b) by 471 days.

(21) Appl. No.: 11/554,550

(22) Filed: Oct. 30, 2006

(65) Prior Publication Data

US 2007/0299463 A1 Dec. 27, 2007

Related U.S. Application Data

(63) Continuation of application No. 10/815,282, filed on Apr. 1, 2004.

(51) Int. Cl.
*A61B 8/12* (2006.01)
(52) U.S. Cl. ...................... 600/116; 606/192
(58) Field of Classification Search ................ 600/116; 606/192
See application file for complete search history.

(56) References Cited

U.S. PATENT DOCUMENTS 3,901,232 A 8/1975 Michaels et al.
5,713,141 A 2/1998 Mitchell et al.
5,738,657 A 4/1998 Bryant et al.
5,883,915 A 3/1999 Kortz
6,082,025 A 7/2000 Bonk et al.
6,352,077 B1 3/2002 Shah
6,460,541 B1 10/2002 Shah et al.
6,663,646 B1 12/2003 Shah
6,712,832 B2 3/2004 Shah
6,733,512 B2 5/2004 McGhan
6,976,950 B2 12/2005 Connors et al.
6,981,980 B2 1/2006 Sampson et al.
2007/0212559 A1 9/2007 Shah

FOREIGN PATENT DOCUMENTS

| JP | 51-090376 A | 8/1976 |
| JP | 51-100833 A | 9/1976 |
| JP | 51-101084 A | 9/1976 |
| JP | 10-127771 A | 5/1998 |

*Primary Examiner*—Thao T. Tran
(74) *Attorney, Agent, or Firm*—Vincent K. Gustafson; Intellectual Property/Technology Law

(57) ABSTRACT

A method of treating a patient comprises: introducing to a physiological locus of said patient a balloon formed from two vacuum thermoformed half-sections of a multilayer film a layer of sealing film and at least one layer of thermoplastic polymer film, wherein the vacuum thermoformed half-sections are bonded together; and the balloon includes an inflation element (such as a self-healing valve and/or an effervescent material) adapted to permit inflation of the balloon at the physiological locus with a fluid.

25 Claims, 2 Drawing Sheets

THERAPEUTIC INTERVENTION SYSTEMS EMPLOYING IMPLANTABLE BALLOON DEVICES

STATEMENT OF RELATED APPLICATION(S)

This application is a continuation of an claims benefit of U.S. patent application Ser. No. 10/815,282, filed on Apr. 1, 2004 and entitled "EXTRUSION LAMINATE POLYMERIC FILM ARTICLE AND GASTRIC OCCLUSIVE DEVICE COMPRISING SAME."

BACKGROUND OF THE INVENTION

1. Field of the Invention

This invention relates to therapeutic intervention methods, such as gastric occlusion methods, employing implantable balloon structures formed of laminate films, and to related therapeutic devices.

2. Description of the Related Art

In the field of polymeric film technology, involving polymeric sheet stock or web-form material, typically having a thickness of less than about 25 mils, there is a need for gas-barrier films.

Such gas barrier films may be employed for containment of a specific gas when used to form gas receptacles, or as a packaging, cushioning or preservative structure (e.g., when fabricated to contain gas species such as oxygen, nitrogen, argon, helium, carbon dioxide, water vapor, etc). Still other applications relate to the prevention or reduction of gas passage through the film, such as in instances in which any significant penetration of gas through the film may adversely impact an article, structure, material or region that is isolated from an adverse gas environment by the gas barrier film.

In the aforementioned applications, the film material may be susceptible to forces and consequent stresses that cause failure of the film, e.g., by cracking, tearing, splitting, stress-softening, embrittlement or other material failure mechanisms.

Specific applications of such gas barrier films may include the requirement of biocompatibility, in which the gas barrier film is required to function in or in connection with a physiological environment, whereby the film may be subjected to exposure to biological fluids, variations of temperature, pressure and pH, etc.

There is presently a compelling need in the art for readily manufacturable, soft and supple yet durable and reliable gas barrier films for manufacture of medical devices as well as a wide variety of other product articles.

SUMMARY OF THE INVENTION

The present invention relates to a gas barrier film, as well as to articles and devices incorporating such gas barrier film.

In one aspect, the invention relates to a method of therapeutic intervention for treatment of a patient in need of such treatment, said method comprising: introducing to a physiological locus of said patient a balloon formed from two vacuum thermoformed half-sections of a multilayer film comprising: (A) a layer of sealing film, having main top and bottom surfaces; and (B) at least one layer of thermoplastic polymer film, disposed along least one of the main top and bottom surfaces of the sealing film; wherein the sealing film has a composition and thickness imparting gas barrier character to the multilayer film and wherein the at least one layer of thermoplastic polymer film alone lacks such gas barrier character; wherein the vacuum thermoformed half-sections are bonded together along peripheral portions thereof to form a peripheral edge; and wherein the balloon comprises an inflation element adapted to permit the inflation of the balloon at said physiological locus with a fluid. The inflation element may include, for example, a self healing valve and/or an effervescent material disposed within the balloon.

In another aspect, the invention relates to a method of therapeutic intervention for treatment of a patient in need of such treatment, said method comprising: introducing to a physiological locus of said patient a balloon formed from two vacuum thermoformed half-sections of a multilayer film comprising: (A) a layer of sealing film comprising any of polyvinylidene chloride and an ethyl vinyl alcohol polymer, having main top and bottom surfaces; laminated between (B) a first layer and a second layer of a thermoplastic polymer film; wherein the sealing film has a composition and thickness imparting gas barrier character to the multilayer film and wherein either of the first layer and second layer of thermoplastic polymer film alone lacks such gas barrier character; wherein the vacuum thermoformed half-sections are bonded together along peripheral portions thereof to form a peripheral edge; and wherein the balloon comprises an inflation element adapted to permit inflation of the balloon at said physiological locus with a fluid. The inflation element may include, for example, a self healing valve and/or an effervescent material disposed within the balloon.

In another aspect, the invention relates to a gas-retentive enclosure comprising a multilayer film, wherein the multilayer film comprises:

a layer of sealing film, having main top and bottom surfaces; and a layer of thermoplastic polymer film, laminated to the layer of sealing film, on at least one of the main top and bottom surfaces;

wherein the sealing film has a composition and thickness imparting gas barrier character to the multilayer film and wherein the layer(s) of thermoplastic polymer film alone lacks such gas barrier character In another aspect, the invention relates to a gastric occlusive device, comprising:

a balloon formed of a multilayer film comprising:

a layer of sealing film, having main top and bottom surfaces;

a layer of thermoplastic polymer film, on at least one of the main top and bottom surfaces of the layer of sealing film;

wherein the sealing film has a composition and thickness imparting gas barrier character to the multilayer film and wherein the layer(s) of thermoplastic polymeric material alone lacks such gas barrier character; and an effervescent material contained in said balloon, and arranged for contact with introduced liquid reactive with the effervescent material to liberate gas for inflation of the balloon.

A still further aspect of the invention relates to a method of therapeutic intervention for treatment of a patient in need of such treatment, such method comprising:

introducing to a physiological locus of a patient in need of such therapeutic intervention a balloon formed of a multilayer film, wherein the multilayer film comprises:

a layer of sealing film, having main top and bottom surfaces; and a layer of thermoplastic polymer film, laminated to the layer of sealing film, on at least one of the main top and bottom surfaces;

wherein the sealing film has a composition and thickness imparting gas barrier character to the multilayer film and wherein the layer(s) of thermoplastic polymer film alone lacks such gas barrier character;

with an effervescent material contained in said balloon, and arranged for contact with introduced liquid reactive with the effervescent material to liberate gas for inflation of the balloon.

As used herein, the term "film" means a material in a sheet or web form, having a thickness of 50 mils (1.270 mm) or less.

As used herein, the term "extrusion laminated" in reference to a film of thermoplastic material means that such film of thermoplastic material is deposited as an extruded melt film on (one or both sides of) the sealing layer film, so that the respective thermoplastic material and sealing layer films are consolidated with one another under elevated temperature conditions. The laminate preferably is formed under process conditions producing substantially uniform thickness of the multilayer film, with a thickness variation across the laminated film desirably being less than 20% and more preferably being less than 15% of the total thickness of the laminate.

Other aspects, features and embodiments will be more fully apparent from the ensuing disclosure and appended claims.

DETAILED DESCRIPTION OF THE INVENTION, AND PREFERRED EMBODIMENTS THEREOF

Figure 1:
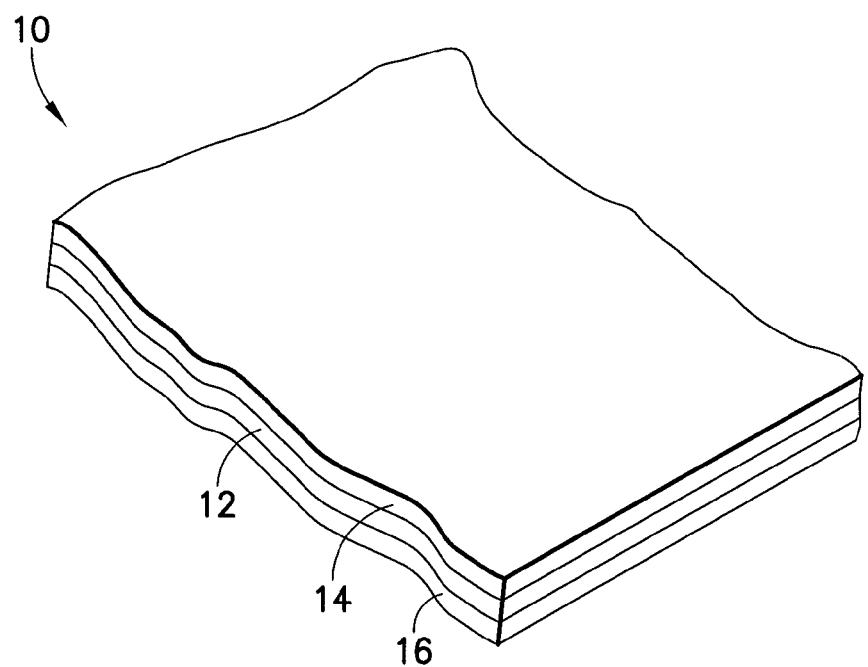
FIG. 1 is a perspective view of a gas barrier film according to one embodiment of the invention.

The present invention is based on the discovery of a laminated multilayer film structure having utility as a gas barrier film, as useful in the fabrication of a wide variety of end-use articles, including, without limitation, gastric occlusion devices.

The disclosures of U.S. patent application No. 09/977,644 filed Oct. 15, 2001 in the name of Tilak M. Shah for "LOW-PRESSURE MEDICAL BALLOONS AND METHOD OF MAKING SAME," and of U.S. Pat. No. 6,712,832 issued on Mar. 30, 2004 from the foregoing application, are hereby incorporated by reference herein in their respective entireties, for all purposes.

The gas barrier film structure of the invention is a laminate including:
 a layer of sealing film, having main top and bottom surfaces; and
 a layer of thermoplastic polymer film, laminated (e.g., extrusion laminated) to the layer of sealing film, on at least one of the main top and bottom surfaces;
 wherein the sealing film has a composition and thickness imparting gas barrier character to the multilayer film and wherein the layer(s) of thermoplastic polymeric material alone lacks such gas barrier character.

The disclosure of U.S. Pat. No. 6,712,832, issued Mar. 30, 2004 in the name of Tilak M. Shah for "LOW-PRESSURE MEDICAL BALLOONS AND METHOD OF MAKING SAME," hereby is incorporated herein in its entirety, for all purposes.

As disclosed in such earlier application Ser. No. 09/977,644, a low-pressure medical balloon can be fabricated by providing a thin film of thermoplastic polymeric material that is heated to a sufficient temperature for vacuum forming thereof. A first half-section for the balloon then is formed by subjecting the thermoplastic polymeric film to vacuum suction. A second half-section for the balloon then is formed by subjecting a same or different thermoplastic polymeric thin film to vacuum suction, following which the first half-section of the balloon is bonded to the second half-section along respective edges thereof to yield the balloon.

Such methodology may be employed to form a low-pressure balloon article of a non-pillowed, generally spherical or flattened spherical character, in which the respective half-sections of the balloon are readily fabricated and mated to form the product balloon article. The balloon article as thus formed may then be everted (turned inside out) so that the free edges (flange or "skirt") of the seam are disposed in the interior volume of the balloon.

The laminate of the present invention is formed with an outer layer (on one or both sides of the sealing film) of a thermoplastic polymeric film material, such as polyurethane elastomer, polyester ether elastomer, polyamide elastomer, etc., having good physical properties for the intended end-use, but which is gas-permeable to an undesired extent, in respect of its intended end-use application. The thermoplastic polymer film may have any suitable thickness, e.g., a thickness in a range of from about 2.0 mils to about 20 mils (0.0508 mm to 0.508 mm), although greater or lesser thicknesses may be employed in specific applications of the invention, e.g., a thickness in a range of from about 2.0 mils to about 5.0 mils (0.0508 mm to 0.127 mm).

The laminate includes a layer of a sealing film. A layer of thermoplastic material is laminated, e.g., extrusion laminated, on at least one of the main top and bottom surfaces of the sealing layer. The sealing film layer has a composition and thickness imparting gas barrier character to the laminated film structure. In other words, the presence of the sealing film effects a diminution of the gas permeability characteristics of the laminate (relative to the gas permeability characteristics of the outer thermoplastic material layer(s) per se), in respect of particular gas components or gas mixtures of interest, so that the resulting multilayer laminate is suitable for use as a gas barrier.

Polyurethane elastomer is a preferred material of construction for the outer layer(s) of the laminated film, although a wide variety of other materials, such as polyester ether elastomer, stryenic elastomers, polyamide and polyamide elastomers and other film-forming thermoplastic elastoplastics, including the polymeric families of polyethylene, polypropylene, polyvinylchloride (PVC), polyvinylether (PVE), ethylene vinyl acetate (EVA) polymers, and combinations of two or more of the foregoing, etc., may be employed. The choice of a specific thermoplastic material for a given end use application, and the choice of extrusion laminating a layer of such thermoplastic material to only one, or alternatively to both, of the surfaces of the sealing film layer, can readily be made within the skill of the art, and without undue experimentation, based on the disclosure herein.

The multilayer laminated film of the present invention is readily processed in the manner described in the aforementioned U.S. patent application Ser. No. 09/977,644, to form balloon and catheter articles of widely varying types.

For example, a multilayer extrusion laminated film of the invention may be utilized to form low-pressure balloons and catheters useful for a wide variety of procedures, such as minimally invasive surgery.

In medical balloon usage, it is important that the balloon structure have uniform wall thickness and concentric expansion during inflation, so that the physiological effect is correspondingly uniform and able to be well-standardized and quantified.

The multilayer extrusion laminated films of the invention are particularly useful in the fabrication of balloon articles such as the gastric occlusive device hereinafter more fully described. In such application, the extrusion laminated film can have a thickness in a range of from about 0.5 to about 10 mils (0.0127 mm to 0.254 mm), and more preferably in a range of from about 2 mils to about 6 mils (0.0508 mm to 0.1524 mm), although greater or lesser thicknesses of the extrusion laminated film may be employed, e.g., a thickness in a range of from 0.5 to about 50 mils (0.0127 mm to 1.27 mm), as appropriate in a specific end-use application.

The sealing film layer, on which at least one outer layer of thermoplastic material is laminated in the laminated film of the invention, may be of any suitable type that is effective to impart gas barrier characteristics to the laminate. As indicated, the outer layer can be formed of a material such as a polyurethane elastomer or other suitable thermoplastic elastomer.

The sealing layer in relation to specific outer layer thermoplastic materials can be fabricated of any complementary material imparting gas barrier characteristics to the overall laminated film that includes the outer layer(s) and the sealing layer. Illustrative sealing layer materials include polyvinylidene chloride (PVDC), commercially available from Dow Chemical Company under the trademark Saran, polyvinylidene bromide, ethylene vinyl alcohol polymers (conventionally referred to as "EVOH" polymers), etc.

The sealing film can be of any suitable thickness as required for the gas barrier end-use application. Typically, when polyvinylidene chloride or EVOH polymers are employed to form the sealing film, the sealing film can have a thickness on the order of from about 0.2 mil to about 6 mil (0.00508 mm to 0.1524 mm).

In an illustrative embodiment, the outer layer of the extrusion laminate is formed of a sealing layer of polyvinylidene chloride, having a thickness in a range of from about 0.25 to about 2.0 mil (0.00635 mm to 0.0508 mm), to which a layer of polyurethane elastomer film, having a thickness in a range of from about 2.0 mils to about 5.0 mils (0.0508 mm to 0.127 mm), is extrusion bonded.

It will be appreciated that when the multilayer laminate of the invention features two outer layers of thermoplastic polymeric material, each laminated to the sealing layer on a respective surface of the sealing layer, the outer layers of thermoplastic material may be the same as or different from one another in composition. For example, a polyurethane elastomeric film may be extrusion laminated to one face of a polyvinylidene chloride film, and a polyethylene film may be extrusion laminated to the other face of the polyvinylidene chloride film.

It will also be appreciated that the thermoplastic material layer may include multiple sub-layers, and that the sealing layer may likewise include multiple sublayers, and that these respective sub-layers may be compositionally homogeneous or alternatively varied in composition along the successive sub-layers.

The laminate of the invention may be utilized to form a gastric occlusive device, as hereinafter more fully described. The gastric occlusive device is a balloon that is fabricated to contain a charge of an effervescent material that in the presence of water or moisture reacts to form $CO_2$ gas. The balloon containing such effervescent material charge can be injected, through the multilayer film via a suitable self-healing seal valve therein, with a requisite amount of water or aqueous medium. The injected water or aqueous medium then reacts with the effervescent material, to generate carbon dioxide as an inflation gas for the balloon.

The balloon of the gastric occlusive device thus is inflated subsequent to being placed in a gastric locus of a patient. The inflated balloon thereafter remains sufficiently gas-tight in character so that the inflated volume of the balloon is relatively constant over an extended period of time.

In one embodiment, the balloon is formed with a degradable seal, which under exposure to a physiological environment degrades to permit deflation of the balloon and removal thereof from a physiological locus.

In one preferred dimensional aspect, the gastric occlusive balloon has a diameter when inflated of 3 to 5 inches, although such balloon in the general practice of the invention may have any suitable size and dimensional characteristics appropriate to the use of the balloon in a specific application thereof.

In a physiological environment, the balloon article of the invention must withstand pressures associated with such environment, e.g., pressures of 1 to 5 psi. Further, the physiological environment may subject the balloon article to compressive, tensile and torsional forces.

Under such conditions in the physiological locus, the multilayer laminate must be resistant to flex-cracking, particularly when such conditions involve repeated cycles of shape-deforming stresses. The selection of film thickness of the laminate is particularly critical in this respect, since excessively thick films are disproportionately more susceptible to flex-cracking, particularly at the seams where adjacent panels or sections of a film are bonded to one another.

Thus, the balloon article incorporates a multilayer laminate that has desired characteristics for the intended use application. These characteristics may variously include softness to the touch (e.g., a Shore D hardness of 65 or less), resistance to flex fatigue, and leak-tightness and dimensional stability under the range of pressure conditions that may be encountered in such intended use application.

Balloon or other gas-retentive or gas barrier articles in accordance with the invention can alternatively be formed using conventional multilayer barrier films, which are processed as described herein. Barrier films including at least one layer of urethane material are advantageously processed as described herein to form balloon articles from half-sections that are produced by vacuum forming, e.g., vacuum thermo-forming, and then bonded at their outer periphery to form a balloon article without openings in the weld line or any other location on the dome of the respective half-sections in the finished article.

Conventional multilayer barrier films of such type may be manufactured either by co-extrusion of sealing layer(s) with outer layer(s), with or without adhesive, or by preformed film of outer layers adhesive laminated to preformed film of sealing layers. For example, co-extruded films of 3-4 layers can be utilized.

Referring now to the drawings, FIG. 1 is a perspective view of an extruded laminate film 10 according to one embodiment of the invention.

The extruded laminate film 10 includes outer film layers 14 and 16 of thermoplastic material, which have been extrusion laminated to a sealing layer film 12.

The outer film layers 14 and 16 of thermoplastic material may comprise a polyurethane elastomer film, or other thermoplastic elastomer film, or any other thermoplastic material film that is gas-pervious in character and by itself has inadequate gas barrier character for the desired end use. The sealing layer, on which the thermoplastic material layers are extrusion laminated, provides a gas barrier film imparting the requisite gas-impervious character to the overall laminate for the intended use application.

While the laminate of FIG. 1 is shown as comprising three layers, i.e., the outer layers of gas-pervious film material and the central layer of sealing film material, it will be recognized that the invention is not limited to such three-layer film constructs, but may comprise two layers, or alternatively more than three layers of material, including at least one outer layer of gas-pervious film and a sealing film layer imparting gas barrier character to the multilayer laminate. In multiple layer laminated films having three or more layers, the additional layers may be formed of any suitable material, to achieve any additional required mechanical or chemical resistance properties, and such additional layers may be extrusion laminated over the sealing film layer and/or outer layer(s), during the fabrication of the laminate.

In a specific embodiment, a three-layer film of the type shown in FIG. 1 includes outer layers 14 and 16 of polyurethane elastomer, having a thickness of about 2 mils (0.0508 mm), and a sealing layer 12 of polyvinylidene chloride film having a thickness of about 1.35 mil (0.0343 mm).

Figure 2:
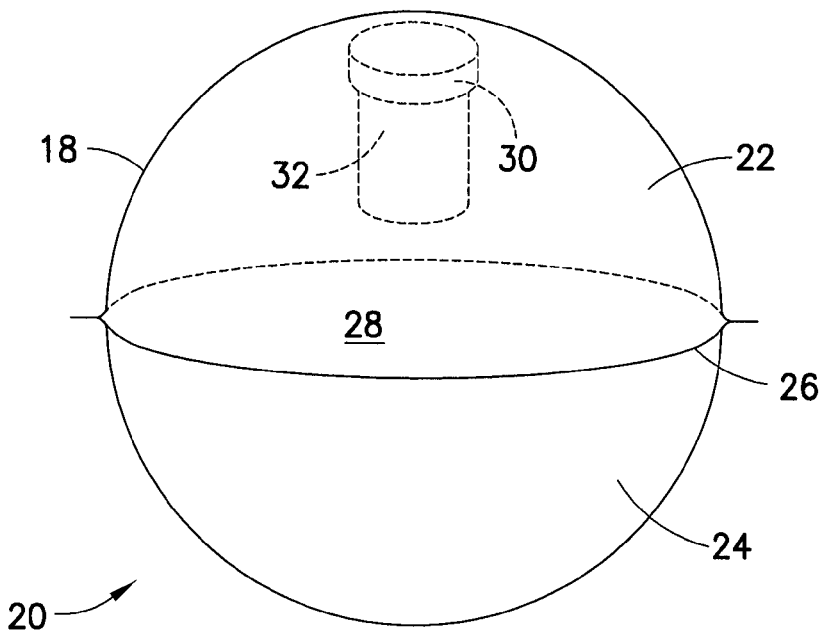
FIG. 2 is a front elevation view of a gastric occlusive device, according to one embodiment of the invention.

FIG. 2 is a front elevation view of a gastric occlusive device, according to one embodiment of the invention.

The gastric occlusion device 20 includes a balloon 18 formed from half-sections 22 and 24, which are joined to one another at edge seam 26 to form an enclosed interior volume 28 of the balloon. The seam 26 may be formed by any suitable type of bonding technique. A preferred bonding technique is radio frequency welding, as discussed hereinafter.

The two pieces of the balloon (half-sections 22 and 24) are preferably bonded circumferentially to one another to form a 360° seal having a seam devoid of any neck or opening therein.

The balloon is shown in its inflated form, in which the interior volume 28 contains a head piece 30 bonded to an inside surface of the upper balloon half-section 22. Joined to the head piece 30 is a gas pill 32 holding an effervescent material. The head piece and laminated film are joined to one another by any suitable bonding means and/or method, and their junction suitably includes a self-healing seal valve through which water or moisture or other aqueous medium may be introduced to contact the effervescent material in the gas pill 32, e.g., from an associated catheter or liquid feed tube (not shown in FIG. 2).

The effervescent material in the gas pill 30 can be of any suitable type that in contact with water, moisture, or physiological media reacts to liberate carbon dioxide or other inflating gas for the balloon, so that the balloon is transformed from an initial collapsed (deflated) state to the inflated state illustratively shown in FIG. 2.

By way of example, the effervescent material can be a mixture of aspirin, sodium bicarbonate and citric acid, or other suitable material generating $CO_2$ in the presence of water, moisture or physiological media.

The balloon may also include a degradable seal if desired, which can be successively deteriorated by a physiological environment in which the balloon is deployed, so that the balloon deflates after a predetermined period of time, and can be more easily be removed, e.g., mechanically or physiologically, from the corporeal locus of deployment.

For example, a degradable seal may be formed of an ethylene vinyl acetate (EVA)/hydroxycellulose blended material that is progressively degradable to create an opening in the balloon after a prolonged period of exposure to a physiological environment, at a thickness permitting the balloon to remain in an inflated state for a period of time sufficient for the desired treatment to be effected. Upon deterioration of the seal, an opening is produced in the balloon that permits the inflation gas to egress, and the deflated balloon may then be readily removed from the corporeal locus in which treatment is being carried out.

Figure 3:
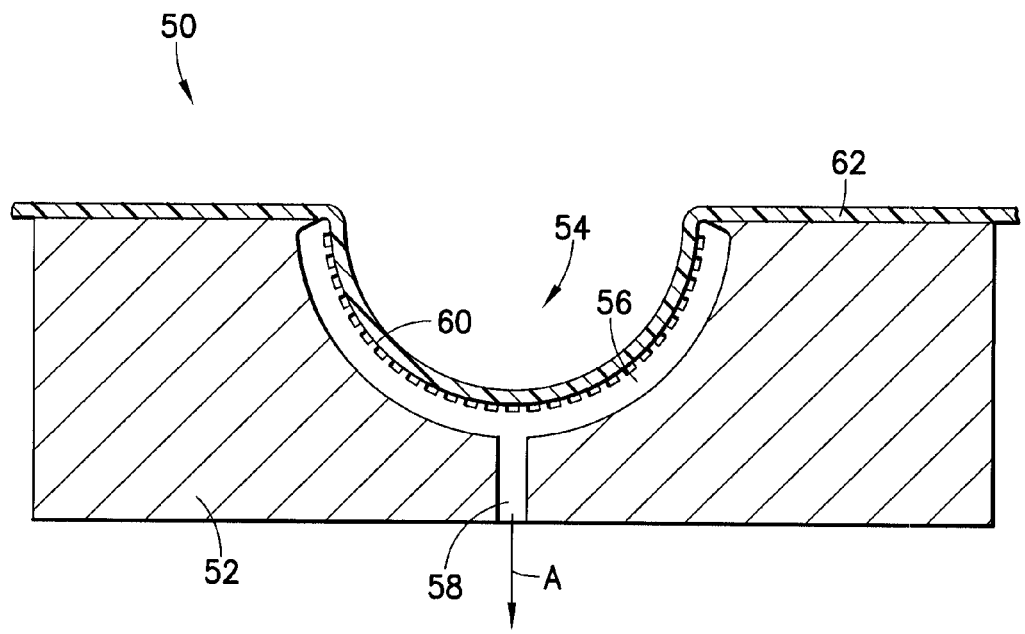
FIG. 3 is a schematic front elevation cross-sectional view of a vacuum thermoforming die for use in forming a balloon article for fabrication of a gastric occlusive device of the type shown in FIG. 2.

FIG. 3 is a front elevation cross-sectional view of a vacuum forming assembly 50 for forming a balloon article of the type shown in FIG. 2.

The assembly 50 includes a thermoforming die 52. The die has a block-like body 52 with a generally hemispherical cavity 54 therein, whose surface 60 communicates through gas withdrawal passages therein with the gas extraction plenum 56. The gas extraction plenum 56 communicates in turn with discharge passage 58. The discharge passage 58 can be coupled with a suitable vacuum source (not shown in FIG. 3), such as a vacuum pump, for extraction of gas from the thermoforming cavity when overlaid by the extrusion laminate film 62. Under the negative pressure imposed by the vacuum source, the central portion of the multilayer film 62 is drawn into the die cavity as shown, against the die cavity surface 60, and the evacuated gas is discharged from the die via the discharge passage 58 in the direction indicated by arrow A.

The extruded laminate film 62 in such processing is at sufficient temperature for vacuum thermoforming, i.e., a temperature above the softening temperature of the thermoplastic polymeric material. Such temperature preferably is above the Vicat softening temperature of the thermoplastic polymeric laminate material, but below the deformation temperature of such laminate material. The Vicat softening temperature of polyurethane elastomers, for example, is usually from about 60° to about 150° C., depending on the nature of the specific polymer involved.

The Vicat softening temperature is readily determinable within the skill of the art without undue experimentation, for any of various other suitable thermoplastic polymeric materials that may be employed in the extruded laminate.

By applying negative pressure to the mold cavity so that the heated and softened thermoplastic polymeric laminate film is induced to conform to the shape of the mold cavity, the laminate is vacuum-molded to the required generally hemispherical shape. In lieu of the female mold structure shown in FIG. 3, a male mold may alternatively be employed to form the respective half-sections of the balloon article.

The first and second half-sections of the balloon can be formed simultaneously, or they may be formed sequentially. The same sheet or web stock of extruded laminate material may be employed for such purpose, or different sheets of thermoplastic polymeric laminates may be employed, as illustrated.

Figure 4:
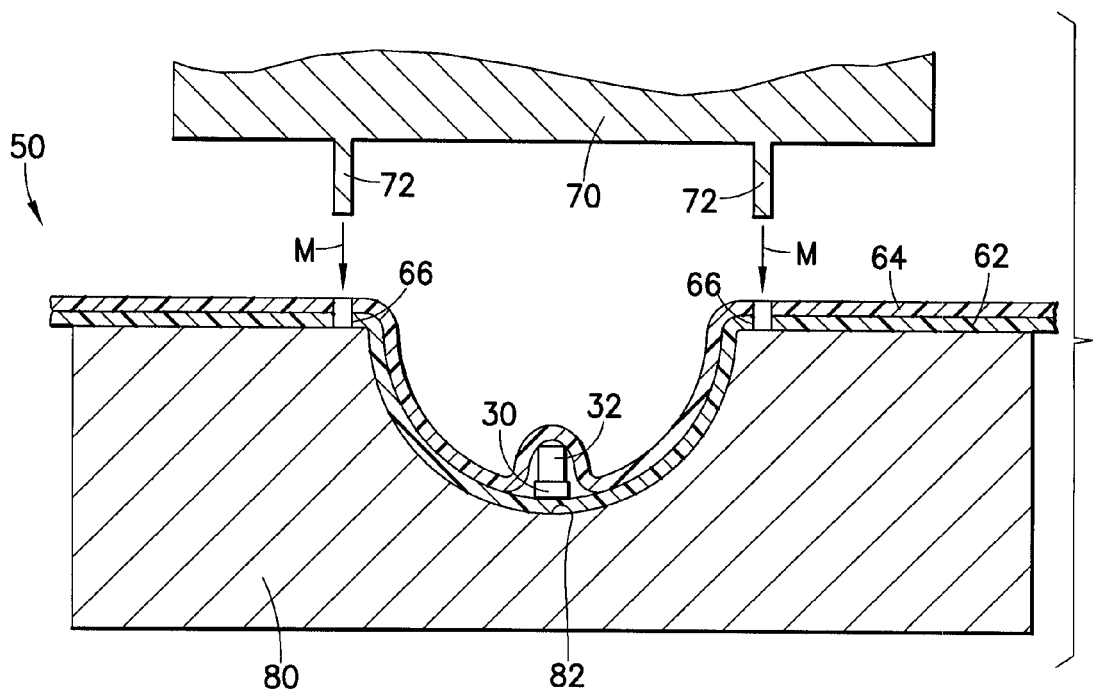
FIG. 4 is a schematic cross-sectional elevation view of a radio frequency (RF) welding operation by which two vacuum thermoformed half-sections formed in the assembly of FIG. 3 after being mated with one another for consolidation at an edge seam, are welded under heat and pressure conditions effecting bonding of the half-sections to one another.

After thermo-vacuum molding two half-sections of the balloon by the arrangement shown in FIG. 3, the half-sections can be superimposed and bonded together at their margins (edges) by any of various suitable bonding methods, as for example the radio frequency welding method that is illustrated schematically in FIG. 4.

FIG. 4 shows a base mold 80 having the superimposed multilayer laminate films 62 and 64 arranged in the cavity 82 so that the generally hemispherical half-sections of such films are in register with one another, with the head piece 30 and gas pill 32 assembly therebetween.

The radio frequency welding die 70 is shown disposed above the base mold 80 and in position for downward translation in the direction indicated by arrows M, to weld films 62 and 64 to one another at the circumferentially extending weld region 66 by contact of the circumferentially extending welding ring 72 with the superposed film layers. Subsequent to such welding, the welded films may be removed from the cavity 82, and the welded sphere can be trimmed adjacent the outer periphery of the weld region 66, to yield the balloon article.

Although radio frequency welding is a preferred technique for bonding of the respective half-sections of the balloon to one another, any of various other suitable bonding techniques may be employed in the broad practice of the present invention, as for example, adhesive bonding, electromagnetic bonding, hot plate welding, impulse heat induction bonding, insert bonding, spin welding, thermostacking, ultrasonic sealing or vibration welding, or various combinations of two or more of the foregoing techniques.

In a preferred aspect, the two half-sections of the balloon are bonded together by radio-frequency welding as described in U.S. Pat. No. 5,833,915 for "Method of Welding Polyurethane Thin Film," issued Nov. 10, 1998 to the present inventor. The disclosure of such patent hereby is incorporated herein by reference in its entirety, for all purposes.

As discussed, the gas pill 32 containing the effervescent material can be secured to an interior surface of the balloon. Alternatively, the gas pill can simply be positioned in an unsecured state in the interior volume of the balloon. This is acceptable, provided that the gas pill is accessible to water, moisture or other medium serving to effect reaction of the effervescent material to produce carbon dioxide or other gas for inflation of the balloon in vivo.

As a still further alternative, the balloon article may be fabricated with a gas supply tube, or otherwise be constructed so that the balloon is able to be inflated at the locus of use, if required to be delivered to such locus in an uninflated state.

The balloon article may additionally be fabricated or adapted so that it is readily removable from the body of the patient, e.g., by means of a hook, loop, vacuum suction head or other engagement structure associated with a catheter, guide wire, or other extraction device. The extraction device in a specific embodiment may be provided with means for puncturing the inflated balloon in vivo to facilitate its removal from the body of a patient.

It will therefore be seen that medical balloon articles are readily fabricated from multilayer laminates in accordance with the present invention, and are suitable for carrying out a wide variety of therapeutic interventions.

It will be appreciated that the laminate film of the balloon may be utilized as a drug delivery device, with the film being coated on its outside surface with a therapeutic agent, e.g., an anti-viral agent, an anti-inflammatory agent, a time-release analgesic formulation, a clotting factor, etc.

The balloon can also in another embodiment be utilized as a gas-retentive enclosure, e.g., as a coolant reservoir in which the gas retained in the interior volume of the balloon is water vapor, or other coolant medium.

Thus, while the invention has been variously described hereinabove with reference to specific aspects, features and embodiments, it will be recognized that the invention is not thus limited, but rather extends to and encompasses other variations, modifications and alternative embodiments, such as will suggest themselves to those of ordinary skill in the art based on the disclosure herein. Accordingly, the invention is intended to be broadly construed and interpreted, as encompassing all such variations, modifications and alternative embodiments, within the spirit and scope of the claims hereinafter set forth.

What is claimed is:

1. A method of therapeutic intervention for treatment of a patient in need of such treatment, said method comprising:
   introducing to a physiological locus of said patient a balloon formed from two vacuum thermoformed half-sections of a multilayer film comprising: (A) a layer of sealing film, having main top and bottom surfaces; and (B) at least one layer of thermoplastic polymer film, disposed along least one of the main top and bottom surfaces of the sealing film; wherein the sealing film has a composition and thickness imparting gas barrier character to the multilayer film and wherein the at least one layer of thermoplastic polymer film alone lacks such gas barrier character; wherein the half-sections are processed in a vacuum thermoforming die, and the vacuum thermoformed half-sections are bonded together along peripheral portions thereof to form a peripheral seam; and wherein the balloon comprises an inflation element adapted to permit the inflation of the balloon at said physiological locus with a fluid; and
   inflating the balloon, yielding a balloon that is non-pillowed and generally spherical or flattened spherical in shape.

2. The method of claim 1, wherein the inflation element comprises a self-healing seal valve adapted to permit the introduction of a fluid into the balloon and retain said introduced fluid within said balloon.

3. The method of claim 2, further comprising introducing said fluid into the balloon through the self-healing valve, and said fluid comprises a liquid or aqueous substance.

4. The method of claim 1, wherein the inflation element comprises an effervescent material disposed within the balloon, the method further comprising contacting the effervescent material with a fluid reactive with the effervescent material to liberate gas for inflation of the balloon at said physiological locus.

5. The method of claim 1, wherein the multilayer film has a thickness of up to about 10 mils.

6. The method of claim 1, wherein the balloon in an inflated state has a diameter in a range of from about 3 inches to about 5 inches.

7. The method of claim 1, wherein each half-section is substantially hemispherical.

8. The method of claim 1, wherein at least a portion of said balloon comprises a degradable material that is degradable in exposure to physiological components in said gastric cavity, said degradable material being adapted to retain the balloon in an inflated state for a predetermined period of time sufficient for said treatment of said subject and to deflate after said period of time by egress of said inflation medium through the degradable material.

9. The method of claim 1, wherein said degradable material comprises an ethylene vinyl acetate/hydroxycellulose material that is progressively degradable in the gastric cavity to create an opening in the balloon for deflation of said balloon.

10. The method of claim 1, wherein the sealing film comprises any of polyvinylidene chloride and an ethyl vinyl alcohol polymer, said at least one layer of thermoplastic polymer film comprises a first and a second layer of polyurethane, said first layer of polyurethane is laminated to the sealing film along the main top surface thereof, and said second layer of polyurethane is laminated to the sealing film along the main bottom surface thereof.

11. The method of claim 1, wherein the two half-sections are bonded circumferentially to one another such that the peripheral edge forms a 360° seal and the peripheral seam is devoid of any neck or opening therein.

12. The method of claim 1, wherein said physiological locus comprises a gastric cavity.

13. The method of claim 2, further comprising introducing, to the physiological locus with the balloon, a fluid supply tube communicatively coupled with the self-healing seal valve.

14. The method of claim 1, further comprising (A) deflating the balloon and (B) extracting or excreting the balloon from the patient.

15. The method of claim 1, wherein the balloon comprises a coating on an exterior surface of the balloon, said coating comprising a therapeutic agent.

16. The method of claim 1, wherein the multilayer film comprises a sealing layer comprising any of polyvinylidene chloride and an ethyl vinyl alcohol polymer, said sealing layer is disposed between a first and a second thermoplastic polymer film layer comprising polyurethane, and said sealing layer comprises an adhesive layer disposed between any of (1) the first thermoplastic polymer film layer and the sealing layer, and (2) the second thermoplastic polymer film layer and the sealing layer.

17. A method of therapeutic intervention for treatment of a patient in need of such treatment, said method comprising:
introducing to a physiological locus of said patient a balloon formed from two vacuum thermoformed half-sections of a multilayer film comprising: (A) a layer of sealing film comprising any of polyvinylidene chloride and an ethyl vinyl alcohol polymer, having main top and bottom surfaces; laminated between (B) a first layer and a second layer of a thermoplastic polymer film; wherein the sealing film has a composition and thickness imparting gas barrier character to the multilayer film and wherein either of the first layer and second layer of thermoplastic polymer film alone lacks such gas barrier character; wherein the half-sections are processed in a vacuum thermoforming die, and the vacuum thermoformed half-sections are bonded together along peripheral portions thereof to form a peripheral seam; and wherein the balloon comprises an inflation element adapted to permit inflation of the balloon at said physiological locus with a fluid; and
inflating the balloon, yielding a balloon that is non-pillowed and generally spherical or flattened spherical in shape.

18. The method of claim 17, wherein the inflation element comprises a self-healing seal valve adapted to permit the introduction of a fluid into the balloon and retain said introduced fluid within said balloon.

19. The method of claim 18, further comprising introducing said fluid into the balloon through the self-healing seal valve, and said fluid comprises a liquid or aqueous substance.

20. The method of claim 17, wherein the inflation element comprises an effervescent material disposed within the balloon, the method further comprising contacting the effervescent material with a fluid reactive with the effervescent material to liberate gas for inflation of the balloon at said physiological locus.

21. The method of claim 17, wherein the thermoplastic polymer film comprises polyurethane.

22. The method of claim 17, wherein each half-section is substantially hemispherical.

23. The method of claim 17, wherein at least a portion of said balloon comprises a degradable material that is degradable in exposure to physiological components in said gastric cavity, said degradable material being adapted to retain the balloon in an inflated state for a predetermined period of time sufficient for said treatment of said subject and to deflate after said period of time by egress of said inflation medium through the degradable material.

24. The method of claim 17, further comprising (i) deflating the balloon and (ii) extracting or excreting the balloon from the patient.

25. The method of claim 17, wherein the multilayer film has a thickness of up to about 10 mils, and the balloon in an inflated state has a diameter in a range of from about 3 inches to about 5 inches.

\* \* \* \* \*

UNITED STATES PATENT AND TRADEMARK OFFICE
CERTIFICATE OF CORRECTION

PATENT NO. : 7,682,306 B2
APPLICATION NO. : 11/554550
DATED : March 23, 2010
INVENTOR(S) : Tilak M. Shah It is certified that error appears in the above-identified patent and that said Letters Patent is hereby corrected as shown below:

Column 1, line 7, "continuation of an claims benefit" should be -- continuation of and claims benefit --.

Column 2, line 39, "gas barrier character" should be -- gas barrier character. --.

Column 3, lines 52-58, "The disclosures of U.S. patent application No. 09/977,644 filed Oct. 15, 2001 in the name of Tilak M. Shah for "LOW-PRESSURE MEDICAL BALLOONS AND METHOD OF MAKING SAME," and of U.S. Pat. No. 6,712,832 issued on Mar. 30, 2004 from the foregoing application, are hereby incorporated by reference herein in their respective entireties, for all purposes." should be -- Thus, while the invention is described more fully hereinafter with reference to an illustrative gastric occlusive device, as fabricated from the laminated multilayer film of the invention, it will be appreciated that the inventive film is susceptible of a wide variety of usages, e.g., in applications in which the film must contain a gas at pressure at least equal to pressure of an ambient environment of the article incorporating such film, or in which permeation of gas through the film would adversely affect a structure, article or material on an opposite side of the barrier film from such gas. --.

Column 4, lines 3-7 should be deleted.

Signed and Sealed this

Sixth Day of July, 2010

David J. Kappos
*Director of the United States Patent and Trademark Office*